United States Patent [19]

Moore

[11] 4,128,664

[45] Dec. 5, 1978

[54] SUBSTITUTED BENZAMIDES AS ANTI-INFLAMMATORY AGENTS

[75] Inventor: George G. I. Moore, Birchwood, Minn.

[73] Assignee: Riker Laboratories, Inc., Northridge, Calif.

[21] Appl. No.: 869,620

[22] Filed: Jan. 16, 1978

Related U.S. Application Data

[62] Division of Ser. No. 797,175, May 16, 1977, abandoned.

[51] Int. Cl.$^2$ ............................................. A01N 9/20
[52] U.S. Cl. ................................. 424/324; 260/559 R
[58] Field of Search ........................................... 424/324

[56] References Cited

U.S. PATENT DOCUMENTS

| 3,932,324 | 1/1976 | Stretanski | 260/23 H |
|---|---|---|---|
| 3,972,927 | 8/1976 | Susi et al. | 260/559 R |
| 3,992,434 | 11/1976 | Oppelt et al. | 260/473 S |

*Primary Examiner*—Stanley J. Friedman
*Attorney, Agent, or Firm*—Cruzan Alexander; Donald M. Sell; Donald C. Gipple

[57] ABSTRACT

Compounds in which 2,6-di(t-butyl)phenol is substituted in the 4 position by an N-substituted carboxamido group have valuable pharmacological activity as anti-inflammatory agents.

8 Claims, No Drawings

SUBSTITUTED BENZAMIDES AS ANTI-INFLAMMATORY AGENTS

This is a division of application Ser. No. 797,175 filed May 16, 1977, now abandoned.

BACKGROUND OF THE INVENTION

This invention relates to certain substituted benzamides and to their use as anti-inflammatory agents. More particularly it relates to certain 2,6-di(t-butyl)-phenols substituted in the 4 position by an N-substituted carboxamido group, the N substitution being alkyl, alkoxyalkyl or allyl, and to the use of such compounds as anti-inflammatory agents.

Such compounds have not been known previously. 2,6-Di(t-butyl)phenol substituted in the 4 position by a carboxamido group which is itself disubstituted by ethanol is known to the art as a polymer stabilizer and/or polymer antioxidant (see, for example, German Offenlegungschrift No. 2,520,725). No physiological use of such compound has been reported, however.

DETAILED DESCRIPTION OF THE INVENTION

Specifically the invention relates to compounds of the formula:

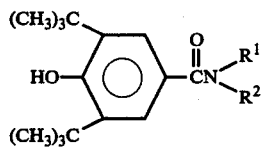

wherein $R^1$ is hydrogen, alkyl or alkoxyalkyl of 1 to 4 carbon atoms or allyl, and $R^2$ is alkyl or alkoxyalkyl of 1 to 4 carbon atoms or allyl, and to a method for combatting inflammatory processes in mammalian animals which comprises adminstering thereto an effective dose, less than the toxic amount, of a compound of formula I. In addition, the invention relates to anti-inflammatory compositions comprising one or more compounds of formula I together with a suitable pharmaceutical extending medium.

A preferred subclass of the compounds of formula I includes those in which $R^1$ is hydrogen. Another preferred subclass includes those compounds of formula I in which $R^1$ and $R^2$ are alkyl of 1 or 2 carbon atoms. Preferably, also, when $R^1$ is not hydrogen, the total number of carbon atoms in $R^1$ and $R^2$ does not exceed 6.

In addition to their anti-inflammatory activity, some of these compounds are also analgesic and antipyretic agents and some have mild immunosuppressant activity.

In order to determine and assess pharmacological activity, testing in animals is carried out using various assays known to those skilled in the art. Thus, the anti-inflammatory activity of the compounds can be conveniently demonstrated using an assay designed to test the ability of these compounds to antagonize the local edema which is characteristic of the anti-inflammatory response (the rat foot edema test). The compounds (I above) have also been found to inhibit the enzyme prostaglandin synthetase and some of them are quite active when administered dermally. Such topical activity has been measured by means of the guinea pig erythema test and by a contact sensitivity test. Anti-inflammatory activity may also be detected by other assays known to the art such as the cotton pellet granuloma test and the adjuvant arthritis test. The analgesic activity has been observed in standard test methods such as the phenylquinone writhing (mouse) and Randall-Selitto (rat) tests.

Leading references to the rate foot edema method are:

(1) Adamkiewicz et al, Canad. J. Biochem. Physio. 33:332, 1955;
(2) Selye, Brit. Med. J. 2:1129, 1949; and
(3) Winter, Proc. Exper. Biol. Med. 111:544, 1962.

The edema test is performed on adult female rats. One group of 10 rats serves as non-medicated controls, while another group of 10 rats receives the test compounds at various times prior to the induction of the edema, usually 15 minutes, one hour and/or 18 hours. The test compound is administered orally as a suspension in 4 percent aqueous solution of acacia. Edema is induced by the plantar injection of 0.5 percent carrageenin (0.1 ml/foot) into the right hind foot. The left hind foot receives a like volume of 0.9 percent saline solution. One hour later, the volume of each hind foot is determined plethysmographically. The edema is expressed as the increase in the volume of the edemogen-injected foot (volume of the "edemogan foot" less the volume of the "saline foot"). The percent inhibition is calculated by dividing the mean increase in the edema of the edemogen foot of the medicated group by the mean increase in the non-medicated group, multiplied by 100. An active dose is that giving a statistically significant inhibition of the induced edema, usually in the range of about 25-35 percent inhibition.

The compounds are preferably administered orally as anti-inflammatory agents but other known methods of administration are contemplated as well, e.g. dermatomucosally (for example dermally, rectally and the like) and parenterally, for example by subcutaneous injection, intramuscular injection, intra-articular injection, intravenous injection and the like. Ocular administration is also included. Dosages ordinarily fall within the range of about 1 to 500 mg/kg of body weight of the mammal to be treated although oral dosages are not usually above 50 mg/kg. Suitable forms for oral administration include liquids (such as 4 percent acacia and polyethylene glycol solutions), tablets (which may contain anhydrous lactose, microcrystalline cellulose, modified starch, calcium stearate and talc, as well as other conventional compounding agents together with the active anti-inflammatory agents), solid suspensions and capsules. Suitable carriers for topical application include creams, gels, tapes and the like. Liquid formulations, such as solutions or suspensions of the active ingredient in inert carriers, are contemplated for dosage by injection.

The compounds which are presently preferred for use in the process of the invention are:
3,5-di(t-butyl)-4-hydroxy-N-methylbenzamide,
3,5-di-(t-butyl)-4-hydroxy-N-ethylbenzamide,
3,5-di(t-butyl)-4-hydroxy-N-butylbenzamide and
3,5-di(t-butyl)-4-hydroxy-N-(2-methoxyethyl)benzamide.

The compounds of the invention are readily prepared by the reaction of amines with the known compound 3,5-di(t-butyl)-4-hydroxybenzoyl chloride. This reaction, which is of a type known to the art, is carried out in an inert solvent such as dichloromethane, optionally with up to 10 percent of a co-solvent such as N,N-dimethylformamide. Reaction temperatures generally used are from about 0° C. to the boiling (refluxing) point of the reaction mixture. Suitable amines are also known or can be prepared by known methods.

The following examples, which are not intended to in any way limit the scope of the invention, are illustrative thereof.

EXAMPLE 1

To a stirred solution of 13.43 g. (0.05 mole) of 3,5-di(t-butyl)-4-hydroxybenzoyl chloride in 50 ml. of dichloromethane is added dropwise 8.77 g. (0.12 mole) of t-butylamine. The mixture obtained is neutralized carefully with 10 percent hydrochloric acid and washed thrice with 200 ml. portions of water. The organic layer is dried, then evaporated under vacuum to provide a white residue. The residue is dissolved in hot benzene-hexane mixture and crystallized to provide 3,5-di(t-butyl)-4-hydroxy-N-t-butylbenzamide, m.p. 207°–208° C.

Using the method of Example 1 the following additional compounds are prepared:
3,5-di(t-butyl)-4-hydroxy-N-methylbenzamide, m.p. 211.5°–212.5° C.
3,5-di(t-butyl)-4-hydroxy-N-ethylbenzamide, m.p. 202.5°–204.5° C.
3,5-di(t-butyl)-4-hydroxy-N-n-butylbenzamide, m.p. 181.5°–182.5° C.
3,5-di(t-butyl)-4-hydroxy-N-(2-methoxyethyl)benzamide, m.p. 133°–134.5° C.
3,5-di(t-butyl)-4-hydroxy-N-allylbenzamide, m.p. 181°–183° C.

EXAMPLE 2

To a stirred solution of 25 g. (0.1 mole) of 3,5-di(t-butyl)-4-hydroxybenzoic acid in 200 ml. of dichloromethane is added 1 ml. of N,N-dimethylformamide and 0.11 mole of thionyl chloride. The mixture is heated at its reflux temperature for 40 minutes, then 0.1 mole of aqueous dimethylamine is added dropwise. The mixture is stirred for three hours and extracted twice with dichloromethane. The dichloromethane extracts are dried then evaporated to provide a residue which is recrystallized from a benzene-hexane mixture. The while solid is dissolved in dichloromethane, washed twice with 10 percent sodium hydroxide solution, then the dichloromethane layer is evaporated under vacuum. The product is recrystallized twice from a benzene-hexane mixture to provide 3,5-di(t-butyl)-4-hydroxy-N,N-dimethylbenzamide, m.p. 173°–174.5° C.

Using the method illustrated in Examples 1 and 2 the following compounds are also prepared:
3,5-di(t-butyl)-4-hydroxy-N,N-diethylbenzamide,
3,5-di(t-butyl)-4-hydroxy-N-ethyl-methylbenzamide,
3,5-di(t-butyl)-4-hydroxy-N-methyl-N-(2-methoxyethyl)benzamide,
3,5-di(t-butyl)-4-hydroxy-N-allyl-N-methylbenzamide.

EXAMPLE 3

Several compounds of the invention are tested in the rat foot edema test at a dose of 100 mg/kg or less and are found to have statistically significant activity. They are:
3,5-di(t-butyl)-4-hydroxy-N,N-dimethylbenzamide,
3,5-di(t-butyl)-4-hydroxy-N-methylbenzamide,
3,5-di(t-butyl)-4-hydroxy-N-ethylbenzamide,
3,5-di(t-butyl)-4-hydroxy-N-n-butylbenzamide,
3,5-di(t-butyl)-4-hydroxy-N-t-butylbenzamide,
3,5-di(t-butyl)-4-hydroxy-N-(2-methoxyethyl)benzamide, and
3,5-di(t-butyl)-4-hydroxy-N-allylbenzamide.

What is claimed is:

1. A method for combatting inflammatory processes in a mammal which comprises administering an effective dose less than the toxic amount of a compound of the formula

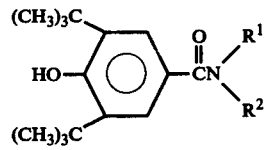

wherein $R^1$ is hydrogen, alkyl of 1 to 4 carbon atoms or alkoxyalkyl of 2 to 4 carbon atoms or allyl, and $R^2$ is alkyl of 1 to 4 carbon atoms or alkoxyalkyl of 2 to 4 carbon atoms or allyl to said mammal.

2. A method according to claim 1 wherein $R^1$ is hydrogen.

3. A method according to claim 1 wherein $R^1$ and $R^2$ are selected from alkyl of 1 or 2 carbon atoms.

4. A method according to claim 1 wherein $R^1$ is hydrogen and $R^2$ is methyl.

5. A method according to claim 1 wherein $R^1$ is hydrogen and $R^2$ is methoxyethyl.

6. A method according to claim 1 wherein $R^1$ is hydrogen and $R^2$ is n-butyl.

7. A method according to claim 1 wherein $R^1$ is hydrogen and $R^2$ is ethyl.

8. A method according to claim 1 wherein $R^1$ and $R^2$ are both methyl.

* * * * *